United States Patent [19]
de Weck

[11] Patent Number: 5,487,977
[45] Date of Patent: Jan. 30, 1996

[54] METHOD FOR THE DETERMINATION OF SULFIDOLEUKOTRIENES IN TISSUES AND BIOLOGICAL FLUIDS AND ITS APPLICATION IN DIAGNOSIS OF ALLERGIES AND OTHER INFLAMMATORY DISEASES

[76] Inventor: Alain L. de Weck, 14, Grand Places, 1700 Fribourg, Switzerland

[21] Appl. No.: 70,326

[22] PCT Filed: Sep. 25, 1992

[86] PCT No.: PCT/EP92/02238

§ 371 Date: Jun. 1, 1993

§ 102(e) Date: Jun. 1, 1993

[87] PCT Pub. No.: WO93/07493

PCT Pub. Date: Apr. 15, 1993

[30] Foreign Application Priority Data

Oct. 1, 1991 [CH] Switzerland ............... 2904/91

[51] Int. Cl.⁶ ............ G01N 33/53; G01N 33/543
[52] U.S. Cl. ............. 435/7.24; 435/7.9; 435/7.1; 435/7.93; 435/7.5; 436/530; 436/531; 436/544; 530/388.2; 530/388.23; 530/388.24
[58] Field of Search ............ 435/7.9, 7.1, 7.24, 435/7.93, 7.5, 975; 436/530, 531, 544; 530/388.2, 388.23, 388.24

[56] References Cited

U.S. PATENT DOCUMENTS 4,559,310 12/1985 Cantor et al. .................. 435/7.21

FOREIGN PATENT DOCUMENTS

| 336647 | 10/1989 | European Pat. Off. ....... G01N 33/88 |
| 3218270 | 11/1983 | Germany ................... G01N 33/56 |
| 61-11663 | 1/1986 | Japan . | |

OTHER PUBLICATIONS

Reinke et al., 1991, A Monoclonal Antibody Against the Sulfidopeptide Leukotrienes $LTC_4$, $LTD_4$, and $LTE_4$.
Harlow et al., 1988, *Antibodies A Laboratory Manual* Cold Spring Harbor Laboratory, pp. 584–587, 591–593, 343.
Johns et al., 1974 Microcalorimetry as a potential tool in the study of antibody–antigen reaction systems incorporating a cellular element I Immunol Meth 4:83–106.
Bischoff et al, 1990, Interleukin 5 modifies histamine release and leukotriene generation by human basophils in response to diverse agonists J Exp Med. 172:1577–82.
Corey, 1982, Chemical studies on slow reacting substances/leurotrienes Experentia 38:1259–75.
Margot Reinke et al., "A Monoclonal Antibody Against the Sulfidopeptide Leukotrienes $LTC_4$, $LTD_4$ and $LTE_4$", *Biochimica et Biophysica ACTA* 1081:274–278, 1991.

Primary Examiner—Toni R. Scheiner
Attorney, Agent, or Firm—Seed and Berry

[57] ABSTRACT

The method for detecting the sulfidoleukotrienes sLT of the group LTC4, LTD4 and LTE4 by a single immunoenzymatic ELISA assay is based on the interaction between one or several monoclonal anti-sLT antibodies and a sLT conjugated to a revealing enzyme. A biological sample, wherein a content of sLT is assumed, is contacted with a monoclonal anti-sLT antibody bound to a carrier. After the sLTs present in the sample are bound to the said antibody, a conjugate of a sLT with a revealing enzyme is added to the charged carrier. Finally the amount of the conjugate bound to the carrier is evaluated, which amount is in an inverse correlation with the sLT bound to the carrier. The method is useful for in vitro-tests for the diagnosis of inflammatory diseases, as rheumatic diseases, immuno deficiencies, allergies or pseudo-allergies. With a priming of the biological samples with cytokines, e.g. with IL3, IL5 or GM-CSF as priming agents, the sensitivity of the method can be increased.

22 Claims, 9 Drawing Sheets

METHOD FOR THE DETERMINATION OF SULFIDOLEUKOTRIENES IN TISSUES AND BIOLOGICAL FLUIDS AND ITS APPLICATION IN DIAGNOSIS OF ALLERGIES AND OTHER INFLAMMATORY DISEASES

The present invention concerns a method for the determination of sulfidoleukotrienes in tissues and biological fluids and its use in the diagnosis of allergies and other inflammatory diseases.

The release of inflammatory mediators by various types of blood or tissue cells upon interaction with various stimulants is a common feature of inflammatory processes occurring in various acute or chronic diseases, such as rheumatic or kidney diseases. In allergic reactions, the release of histamine by blood basophils and/or tissue mast cells has long been considered a major feature. The determination of histamine in supernatants from suspensions of isolated blood leukocytes from allergic patients in vitro, following interaction with allergens to which they are sensitive, is a procedure which has been extensively used in allergy research. However, the fact that such determinations require numerous manipulations, cannot be effected in whole blood, but only on isolated cells, and that histamine determination requires cumbersome and expensive fluorometric or radio-immunoasssays have prevented up to now the routine diagnosis of allergies to rest upon blood cellular assays.

The only current diagnostic method in vitro widely used is the serologic determination of allergen-specific IgE antibodies, by various types of radio-immunological or immunoenzymatic assays (e.g. RAST assay). Such assays, however, only detect the occurrence of antibodies, but do not reflect the most relevant pathophysiological feature of the allergic reaction, namely the production of inflammatory mediators by the reactive cells upon interaction with the responsible allergen(s). For that reason, practical and fiable cellular assays would be most desirable for the routine diagnosis of allergic and other inflammatory diseases. The object of the present invention is to provide a series of novel cellular assays enabling to achieve that purpose.

The sulfidoleukotrienes (sLT) LTC4, LTD4 and LTE4 are inflammatory mediators, which were previously collectively denominated Slow Reactive Substance of Anaphylaxis (SRS-A). They are synthesized in many cell types, such as tissue mast cells, blood basophils, macrophages, eosinophils and kidney mesangial cells. They play an important role in pathological events of inflammation and allergic reactions, particularly in IgE-mediated allergic reactions (Schleimer et al. J. Allergy clin. Immunol., 74, 473–481, 1984). It is of particular interest that blood basophils generate sLT in response to allergens in an IgE-dependent manner (Mita et al. Prostaglandins, 869–886, 1986), and that such basophils generate sLT in response to non-specific stimulants when pre-treated with the cytokines IL-3, IL-5 and GM-CSF (Bischoff et al. J. Exp. Med. 172, 1577, 1990). Theoretically, therefore, on the basis of current knowledge, determination of basophil sLT production in response to suspected non-specific stimulants could be of interest in the diagnosis of allergies. In practice, however, this goal has not yet been achieved, essentially because of multiple technical difficulties. According to the present invention a method is provided which comprises a combination of various, in part novel and original features, by which a routine in vitro cellular diagnostic assay for allergies and other inflammatory diseases can be established.

The subject of the present invention is thus a method for detecting the sulfidoleukotrienes sLT of the group LTC4, LTD4 and LTE4 by a single immunoenzymatic ELISA assay, based on the interaction between one or several monoclonal anti-sLT antibodies and a sLT conjugated to a revealing enzyme, which method is characterized in that a biological sample, wherein a content of sLT is assumed, is contacted with a monoclonal anti sLT-antibody bound to a carrier, the sLT present in the sample are bound to the said antibody, subsequently a conjugate of a sLT with a revealing enzyme is added to the charged carrier and eventually the amount of the conjugate bound to the carrier is evaluated, which amount is in an inverse correlation with the sLT bound on the carrier.

A further subject of the present invention is an application of the above-defined method for diagnostic in vitro tests for the diagnosis of inflammatory diseases.

A further subject of the present invention is a kit of reagents for carrying out the method, which kit comprises a microtiter plate having wells which are coated with monoclonal anti-sLT antibodies, and a conjugate of a leukotriene with a revealing enzyme.

Such an assay involves the following steps:

I. Optimal Enhancement of the Reactive Capacity of Blood Leukocytes, in Particular of Basophils, by Pretreatment with Priming Agents It has been described by the group of the inventor that preincubation for a relatively short time, e.g. incubation (5–10 minutes) of blood leukocytes with a special group of cytokines, namely IL-3 (interleukin 3), IL-5(interleukin 5), GM-CSF (granulocyte/monocyte colony stimulating factor) or NGF (nerve growth factor) has the effect to considerably enhance the capacity of these cells to produce and release mediators, when challenged with appropriate stimulants, such as allergens (for leukocytes of sensitized allergic patients) or non-specific mediator-releasing factors such as complement components C5a and C3a, various basic peptides or bacterial-derived structures, such as formyl-methyl-peptide (fMLP). This phenomenon has been described as "priming".

However, all experiments up to now have been performed on isolated mononuclear leukocytes obtained by gradient centrifugation, a procedure which is cumbersome and possibly eliminates some of the cellular reaction partners also involved, such as monocytes and platelets, as well as some of the blood plasma factors which may influence the outcome of the reaction.

The inventor has now achieved similar results by pretreatment of whole leukocytes or diluted whole blood with purified human recombinant cytokines or with appropriately prepared supernatants of cultures from activated lymphoid cells. Since maximal priming is required for obtaining high sensitivity and release of sLT from the smallest possible number of blood cells and volume of blood, the preferred conditions for achieving priming in whole diluted blood, as described in Example 3, are of utmost importance for the final performance of the test and for its applicability to routine diagnosis.

II. Stimulation of Blood Leukocytes to Production of sLT by Specific Allergens in the Detection of Allergies Following appropriate pretreatment and "priming", as described above, the blood leukocytes, either isolated by gradient centrifugation or other techniques known in the art, or as a suspension in whole diluted blood, are set up in the presence of specific allergens (such as pollen extracts, house dust mite extracts etc.) in a suitable medium for a period of several minutes to one hour.

In a classical experimental set up, as described in Example 3, the blood leukocytes of a putative allergic patient are set up with various doses of allergen extract in fluid form. After the required period of incubation, the cells are centrifuged and the supernatants harvested and analyzed separately for the amount of sLT produced in the sLT ELISA assay described below. This method, however, is inconvenient for a routine diagnostic technique, since it involves multiple manipulations, including the use of several doses per allergen and one centrifugation step.

Surprisingly it was found that for appropriate stimulation of the cells and production of sLT by cytokine-primed blood leukocytes, the allergens may also be provided to the cells as bound to a solid phase. This may be achieved either by adsorption and binding of the allergen to the plastic or nitrocellulose bottom of a microtiter plate, or in the form of an allergen-coupled cellulose disk, similar to those used in the serological RAST assays for allergen-specific IgE antibodies. Appropriate binding conditions, in order to obtain high allergen concentrations per surface unit, such as made possible by pretreatment of the solid surface with glutaraldehyde or polylysine, by a biotin-avidin coupling system or by covalent coupling reagents, are to be preferred. In this way, a unique practical advantage is obtained, in that a single dose incubation with allergen is required in order to obtain optimal production and release of sLT to be measured in the cell supernatant.

Similar procedures may be used for detecting the production of sLT under other circumstances and for the diagnosis of diseases other than IgE specific allergy. For example, the capacity of blood leukocytes to produce sLT when challenged with a number of non specific stimulants, such as component components C5a or C3a, as well as with bacterial structures like fMLP (see Example 5) may be used for evaluating the reactive capacity of the blood cells in various types of immunodeficiencies and of inflammatory diseases, like rheumatic diseases. The spontaneous production of sLT by blood or tissue cells, including biological fluid (e.g. synovial fluid, urine) may be used for assessment of inflammatory disease activity. In that case, it may be necessary first to concentrate the sLTs by extraction or passage on an adsorption chromatography column.

In a similar way, the new tests may also be used for the diagnosis of so-called pseudo-allergies, in which inflammatory cells produce the same mediators than in IgE-mediated allergies but where the triggering mechanism is different. A classical example is the intolerance reactions to aspirin and other non steroidal anti-inflammatory drugs (NSAIDs). In that case, the drugs are inducing the production and release of histamine and sLT in intolerant patients by some other mechanism than IgE-E mediated basophil activation. The precise mechanism is, however, not yet known. The whole blood, encompassing all possible reactive cells, offers a medium mimicking the in vivo situation. In intolerant patients, the addition of aspirin or NSAIDs to whole leukocytes or to whole blood suspensions brings about the production of sLTs, which can be detected in the new assay (see Example 3, FIG. 8). In this way, and for the very first time, this new assay offers a possibility to diagnose pseudo-allergies in vitro. Up to now, the only possibility to confirm a suspicion of pseudo-allergy was to administer the suspected drug or agent to the patient for an in vivo provocation test, a procedure which is inconvenient and may even be dangerous for the patient. The new sLT test also offers the possibility to explore for diagnostic purposes a number of other allergies and pseudo-allergies, hitherto difficult or impossible to detect in vitro, such as intolerance reactions to foods and food additives, drugs and other chemical agents, air pollutants, etc.

III. Detection of sLT

A key element in the new assays is the method developed for assessing all sLTs quantitatively in a single easy-to-perform immunoenzymatic assay.

Up to now, the preferred analytical methods for the determination of leukotriene (LT) concentrations in biological material have been High Pressure Liquid Chromatography (HPLC) and Radioimmunoassay (RIA). The advantage of the HPLC method is that seceral LTs may be determined in one assay. This is, however, outweighed by the disadvantage that the detection is limited to the nanogram range and that every sample has to be purified extensively before being applied to HPLC. This precludes HPLC as a routine diagnostic method. In contrast, the RIA is a very sensitive analytical method and may be used without any purification of samples, such as serum, plasma or cell culture supernatants. The RIA, however, has the disadvantages of using radioactive reagents, an increasingly objectionable procedure, encompassing high production costs. Furthermore, up to recently, only polyclonal antibodies of sufficient affinity and avidity for LT have been available for such assays. In particular, only a few polyclonal antibodies of high specificity for LTC 4 have been described (Lindgren et al., (FEBS Lett. 152, 83–88, 1983; Wynalda et al. Anal. Chem. 56, 1862–1865, 1984).

Decisive progress has been made possible by the availability of monoclonal antibodies strictly specific for LTC4, the primary sLT produced by activated cells, and LTD4 and LTE4, which are the main metabolites of LTC4 (Reinke et al., Biochim. Biophys. Acta, 1081, 274–278, 1991). In this way, it has become possible to assess all relevant sLT products of activated cells in a single radioimmuno- or immunoenzymatic assay. With such a monoclonal antibody, an ELISA assay has recently been described (Reinke et al., Biochim. Biophys. Acta, 1081, 274–278, 1991). In this assay, LTE4 is conjugated to bovine serum albumin, and coated to the wells of a microtiter plate. Biotinylated anti-sLT monoclonal antibody is reacted with the analytical sample containing sLT, followed by incubation in the microtiter plate coated with LTE4-BSA and revelation with avidin-coupled peroxidase. This procedure has several disadvantages for a routine assay: a) its sensitivity is not optimal (about 100 pg), requiring thereby larger quantities of cells: b) the preparation of the reagents is cumbersome and their stability suboptimal; c) the amounts of expensive synthetic LTE4 required are quite large; d) accuracy is not satisfactory when using samples with high protein loads, such as biological and tissue fluids.

This led us to search for alternative ELISA procedures aimed at increasing sensitivity, reducing manipulation steps, improving preparation and quality of the reagents as well as enabling the performance of sLT assays in biological fluids. This modified procedure, as described below, is part of the present invention.

The enclosed drawings and diagrams as well as the appended examples illustrate the present invention.

In summary, the monoclonal anti-sLT antibody is coated onto microtiter plates, or strip devices or other solid phases such as nitrocellulose membranes, without any modification, either directly, with the help of coating agents such as glutaraldehyde or to polylysine, or of a biotin-avidin coupling system, or indirectly with the help of an anti-mouse IgG antibody. Upon incubation of the analytical sample with such a coated microwell (FIG. 1A and 1B), sLTs produced by the cells are directly bound. The revealing step of the assay is provided by mere addition of an LTD4- or LTE4- alkaline phosphatase conjugate, the binding of which is inhibited in direct correlation to the amount of sample sLT bound. Such a simplified sLT inhibition ELISA assay requires substantially less synthetic leukotriene for conjugate production, shows improved sensitivity and reagent stability, and allows simple and effective determination of sLT generated by small numbers of basophils in whole blood.

Precise description of the assays and of their application for diagnostic purposes are given in the following examples. The technical conditions reported are of general character, and should not be considered restrictive, within the boundaries set for achieving the goal pursued, namely suitable and accurate reagents and assay conditions.

EXAMPLE 1

Preparation of LTD4 or other sLT Conjugate with Immunoenzyme, such as Alkaline Phosphatase, Horse-radish Peroxidase or Cholinesterase Synthetic LTD4 was conjugated to glutaraldehyde-activated alkaline phosphatase (AP) (0.2% glutaraldehyde and 175 nM in phosphate buffer saline pH 7.4) for 2 hr at room temperature. The conjugate was then dialyzed overnight at 4° C. or purified by FPLC. After dialysis or FPLC purification, 1% BSA (w/v) was added and the preparation of LTD4-AP was stored in aliquots.

Figure 2:
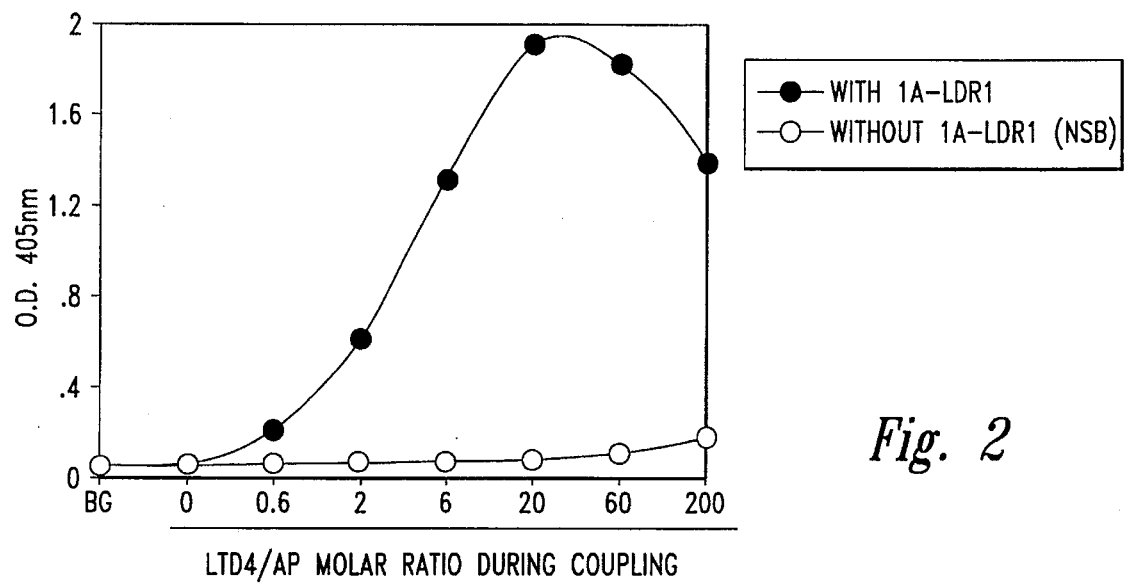
FIG. 2 shows in a diagram the capture of phosphatase from LTD4/AP reaction mixtures by solid phase monoclonal anti-sLT antibody.

Variations in the amount of LTD4 used for the coupling reaction lead to different LTD4 /AP ratios, and lead to differences in the amount of phosphatase activity picked up by anti-sLT antibody (FIG. 2).

Diagram of FIG. 2: AP solution was reacted with increasing amounts of LTD4 in the presence of glutaraldehyde. To detect phosphatase-bound LTD4, reaction mixtures were incubated with anti-sLT moAb 1A-LDR1 (final dilutions 1/25 and 1/500, respectively) in GaM-coated microwells (1 μm/well) for 4 hours at 4° C. (solid circles). Non-specific binding was determined in a similar way but with omission of anti-sLT antibody (open circles). After 3-fold washing with PBS, the phosphatase substrate pNPP was added and optical density at 405 nm was measured after 4 hours at 37° C. Data are duplicate means (variability range <15%). BG indicates the spontaneous hydrolysis of pNPP alone.

It has been found experimentally that conjugate ratios of LTD4/AP ratios of 4:1 to 20:1 are optimal for performance of the assay in terms of sensitivity. Such conjugates show practically no unspecific binding to microtiterplate wells not coated with anti-sLT antibody and therefore a very low background in the sLT assay. Such conjugates have also been found to be stable for over 6 months under appropriate storage conditions.

EXAMPLE 2

Set up and Validation of an sLT-AP Based sLT ELISA Assay

As indicated above, microtiterplate wells or other solid phase recipients known in the art, such as nitrocellulose membranes, may be coated directly with anti-sLT antibody, possibly with the help of binding agents such as glutaraldehyde or polylysine or of a biotin-avidin coupling system. A preferred method, however, is to coat the well with a mixture of anti-mouse IgG antibody and anti-sLT antibody since this considerably increases sensitivity and reduces the amount of anti-sLT antibody required per well. After appropriate coating of the microwells, the analytical sample and a fixed amount of LTD4-AP conjugate are added and incubated for periods which may vary from 30 minutes to 4 hours at 4° C. Following washing, bound phosphatase is revealed by incubation with para-nitrophenyl phosphate (pNPP) (1 mg/ml) added and incubated for 1 to 4 h at 37° C. in phosphatase detection buffer (diethanolamine 97 ml, $MgCl_2.6H_2O$: 100 mg; sodium azide 0.2 g per 1000 ml $H_2O$; pH 9.8). The optical density of the solution at 405 nm is then measured by an appropriate densitometer.

Figure 3A:
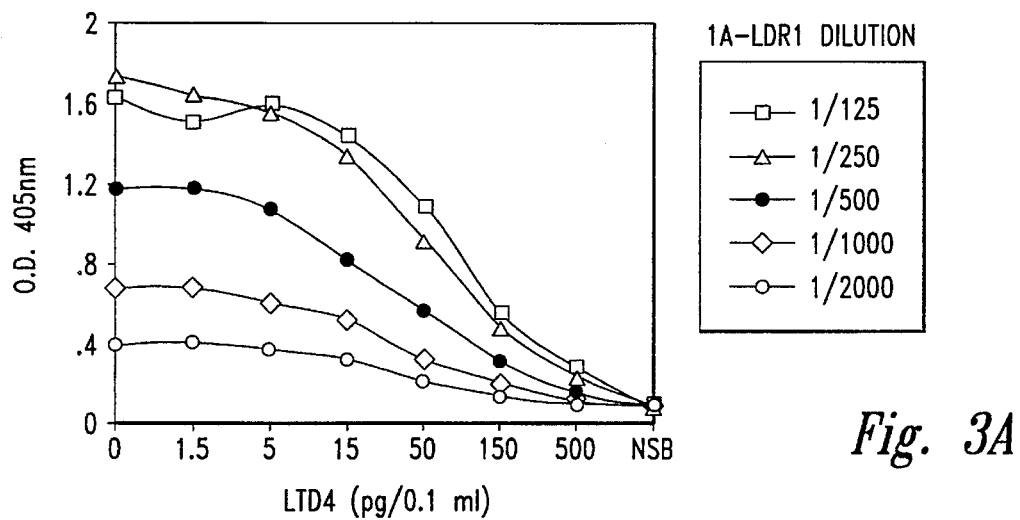
FIGS. 3A and 3B show in a set of two diagrams the LTD4 detection by inhibition ELISA using different combinations of (LTD)-AP and anti-sLT antibody.
Figure 3B:
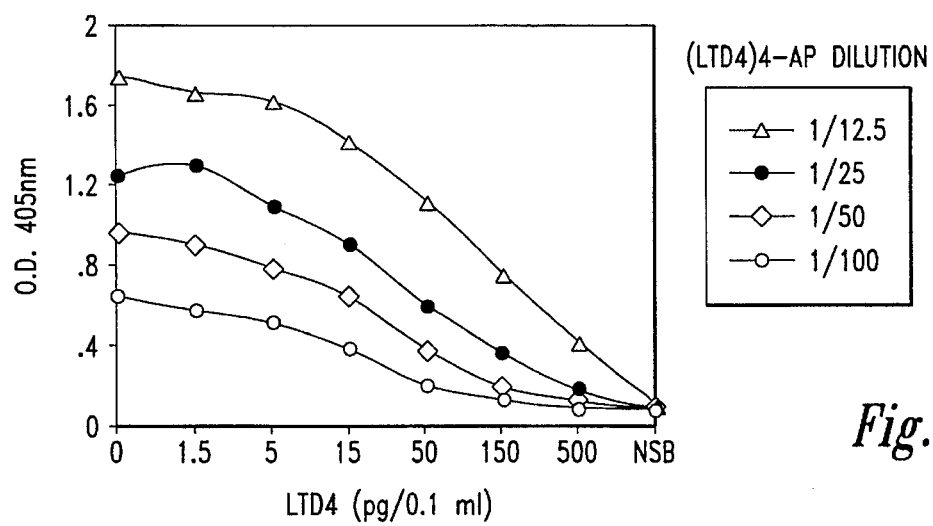

As shown in FIGS. 3A and 3B, optimal conditions for the sLT ELISA test may be found by varying the amounts of anti-sLT antibody coated and the amount of LTD4-AP conjugate used for revelation.

Diagrams of FIG. 3: FIG 3A shows the effect of varying concentrations of anti-sLT moAb 1A-LDR1 at a constant amount of (LTD4)4-AP (final dilution 1/25), FIG. 3B shows inhibition curves obtained with different amounts of(LTD4)4-AP at a fixed dilution of anti-sLT moAb 1A-LDR1 (1/500). NSB indicates non-specific binding of (LTD4)-AP, i.e. in the absence of anti-sLT antibody. Data are means of duplicates (variability range <15%)

Under the conditions of FIG. 3, the lower detection limit was 6 pg LTD4/100 μl sample and 50% inhibition of the standard LTD4 curve was obtained around 65 pg LTD4. This represents an over 10-fold increased sensitivity over the only related sLT-ELISA reported so far (Reinke et al. Biochim. Biophys. Acta. 1081, 274–278, 1991) and a 40-fold decrease in the amount of expensive synthetic sLT reagent required for the assay. The important practical consequence of such an increase in sensitivity is that multiple assays, for example the detection of reactions of the patient's blood cells to several different allergens, may be performed with much smaller blood samples, such as 5 µl to 1000 µl (e.g. 25 µl blood per assay, see Example 4). With less sensitive assays, the amounts of blood required for routine diagnosis become prohibitive.

Figure 4:
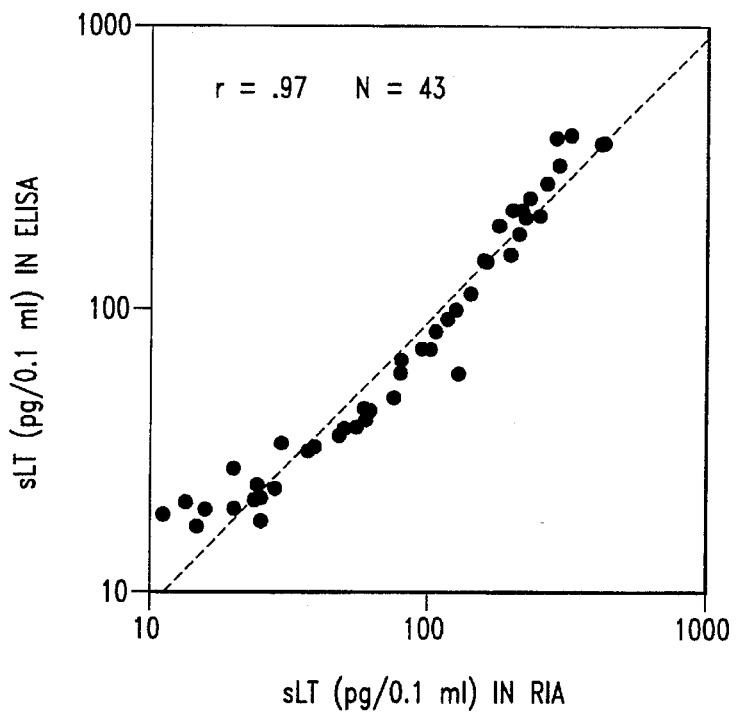
FIG. 4 shows in a diagram the correlation of sLT-measurement by ELISA and RIA.

The absolute sensitivity of the assay can still be increased by modifying the conditions of conjugation of LTD4 to AP, for example by using polymerized AP and/or by selecting optimal conjugate fractions through FPLC purification. The signal generation step may also be enhanced, for example by using a luminogenic phosphatase detection reagent (e.g. AMPPD) in conjunction with microtiter luminescence imaging (Maly et al. Anal. Biochem. 168, 462–469, 1988) or by employing enzyme amplification with the NADP/alcohol dehydrogenase-diaphorase p-iodonitrotetrazolium violet system (Self, J. Immunol. Methods 76, 389–393, 1985). The aim of the present invention being to provide a possibly simple and inexpensive method for routine diagnosis of allergies through an sLT ELISA assay; the conditions described in Examples 2, 3 and 4 represent, however, the nearest optimal solution hitherto found. In a test for the determination of the correlation of sLT measurement by ELISA and RIA, the amounts of sLT in ionomycin-stimulated MNCs supernatants were measured by ELISA (y-axis) and RIA (x-axis). As shown in FIG. 4, the sensitivity of the sLT-ELISA assay is of the same order as that of the best RIA available, and the results correlate very well with those obtained with an RIA, at a fraction of the cost and without the inconveniences caused by the RIA (environmental hazards, short reagent shelf life).

EXAMPLE 3

Two Step Assay for the Detection of sLT Generated by Allergen-exposed Isolated Mononuclear Cells or Diluted Whole Blood by ELISA In the two step assay (FIG. 1A), basophil-containing mononuclear cell suspensions, leukocytes or diluted whole blood are distributed in aliquots in a first series of containers (test tubes or microtiterplate wells), pre-treated with appropriate cytokines such as IL3, IL5 or GM-CSF and then left to interact with allergens provided either in a fluid phase or as bound to some solid phase. After incubation, the containers are centrifuged and the supernatants harvested. These supernatants are then analyzed for sLT content in a second series of containers, usually microtiterplate wells coated with anti-sLT antibody and treated for an sLT-ELISA as described in Example 2.

For preparation of basophil-containing peripheral blood mononuclear cell suspensions (MNC) blood anticoagulated with 10 mM EDTA is mixed with 0.25 volumes of 6% dextran and the erythrocytes allowed to sediment for 90 minutes at room temperature. Leukocytes are pelleted from the supernatant by centrifugation (150 g, 20 min at room temperature) and resuspended in HA buffer (20 mmol Hepes, 125 mmol NaCl, 5 mmol KCl, 0.5 mmol glucose and 0.025% BSA). The cells are then further fractionated by Ficoll-Hypaque density gradient (specific gravity 1.077) centrifugation (600 g, 40 min at room temperature). MNC are harvested from the interphase, washed 3 times (150 g, 10 min at 4° C.) in HA buffer and are finally resuspended in HACM buffer (HA buffer supplemented with 1 mmol $CaCl_2$ and 1 mmol $MgCl_2$) at a cell density of $10^7$ or $5 \times 10^6$ cells/ml. Alternatively, dextran-sedimented leukocytes may be used directly, without washing, following centrifugation and resuspension in HACM buffer.

For generation of sLT by leukocytes or mononuclear cells, 100 µl/well of cell suspension in HACM buffer are heated at 37° C. for 10 min in flat-bottomed microtiter plates. IL 3 or GM-CSF (50 µl, final concentration 10 ng/ml) or HACM buffer are added either simultaneously or for 10 min before adding the stimulant (50 µl, allergen extract or non-specific stimulant such as C5a or fMLP). The reaction is stopped 30–40 min after the addition of stimulants by cooling the microtiterplate on ice. After centrifugation (600 g, 5 min at 4° C.), 100 µl of supernatant are transferred into the ELISA assay microtiter plate and assayed for sLT as described in Example 2.

Figure 5:
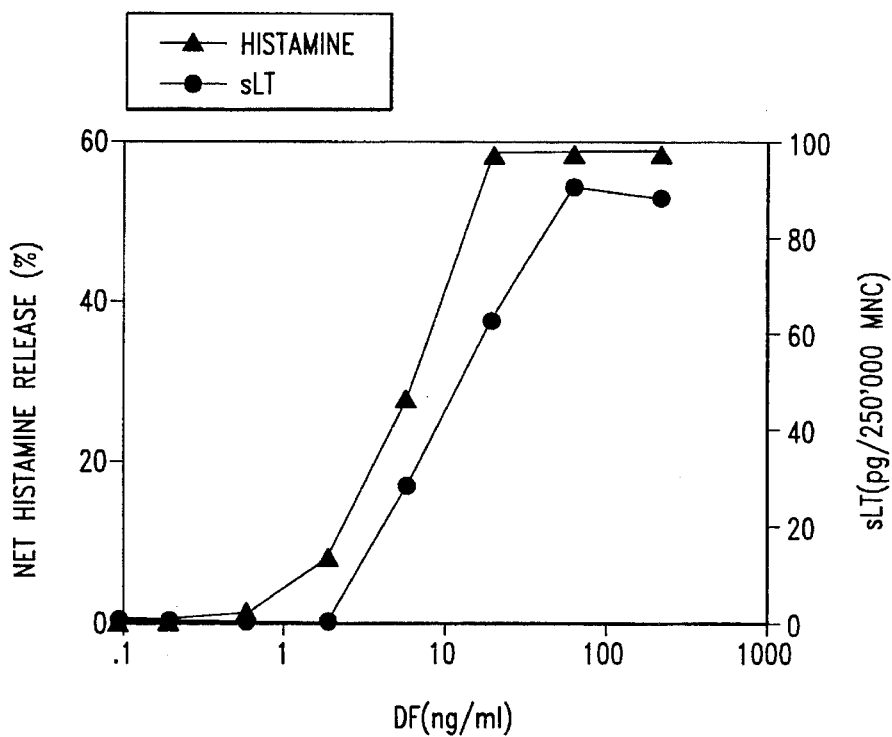
FIG. 5 shows in a diagram the allergen triggered sLT generation and histamine release of isolated human mononuclear cells (MNC).

The diagram of FIG. 5 shows the allergen triggered sLT generation and histamine release of isolated human mononuclear cells (MNC). MNC ($2.5 \times 10^5$/well) from a mite allergic donor (A.U.) stimulated in microtiter wells with increasing amounts of Dermatophagoides farinae allergen (DF). Supernatants were harvested after 40 minutes, and generation of sLT and release of histamine were determined by ELISA and RIA, respectively, as detailed in this specification. Spontaneous histamine release was 1.2%. Data are duplicates means (variability range >15%)

As shown in FIG. 5, the isolated MNC (250'000/microwell) of an individual allergic to the house dust mite *Dermatophagoides pteronyssinus* generate sLT in response to increasing doses of the relevant allergen. These sLT were easily detected by sLT-ELISA and their release was accompanied by a correlated release of histamine. Since MNC contain about 1% basophils and as only 100 µl of the total incubate (250 µl) are used for sLT measurements, the sLT-ELISA detects generation of sLT from about 1000 basophils. Changing incubation volume and supernatant volume used for sLT-ELISA may allow working with even less mononuclear cells.

However, for clinical routine applications, the practicability of the sLT assay would be much improved if isolation of mononuclear cells could be bypassed and the test performed directly in whole blood. Surprisingly, the inclusion of blood plasma proteins in the sLT-ELISA assay does not markedly affect sLT recovery in the sLT-ELISA assay and varies from 70–90% depending upon the plasma concentration. Therefore, detection of sLT generated in diluted whole blood upon stimulation of allergen appeared feasible.

For this assay, venous whole blood is drawn into suitable closed containers with heparin (final concentration 12 U/ml). 100 µl per well of heparinized blood diluted 1:4 with HACM buffer are pipetted into microtiter plates, after which the procedure is exactly as described above for isolated mononuclear cells. The allergen *Dermatophagoides pteronyssinus* stimulates release of sLT in diluted whole blood from a mite allergic individual. In contrast, an irrelevant allergen, *Phleum pratense*, to which this individual is not allergic, does not cause significant release of sLT, even in cells preincubated with IL3. The specificity of the mite allergen-induced sLT generation is further demonstrated by the fact that non allergic individuals show no sLT generation when challenged with either allergen, with or without IL 3 "priming".

For this test, only 25 µl of whole blood are required, which is eminently suitable for multiple routine assays in the same individual.

Figure 6A:
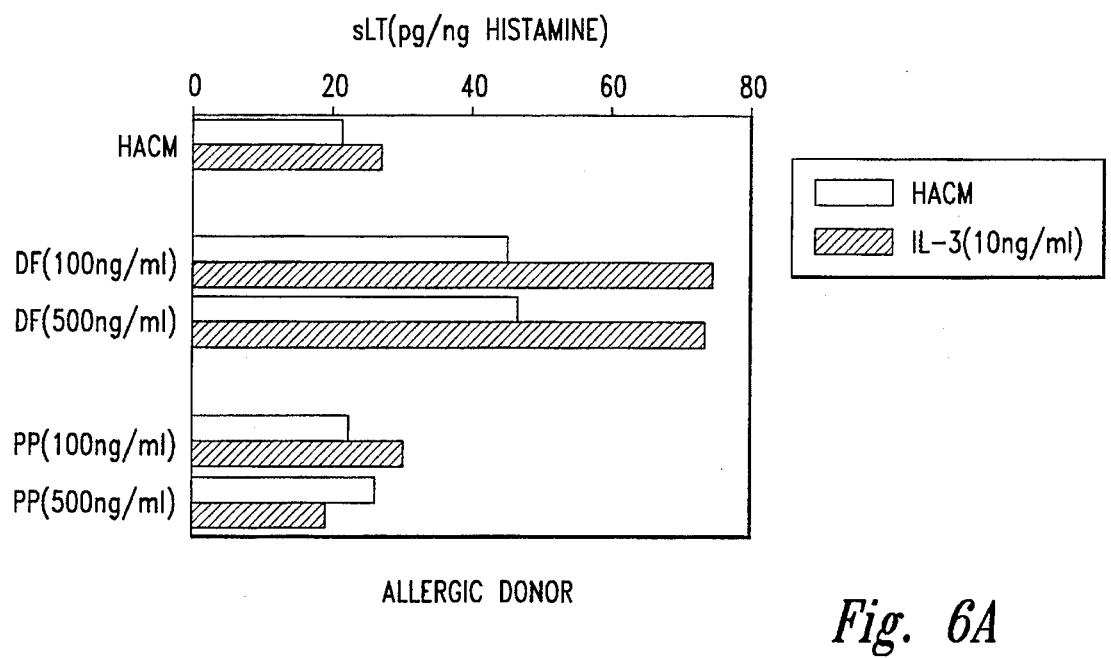
FIGS. 6A and 6B show in a set of two diagrams the ELISA detection of allergen-triggered-sLT generation in diluted whole blood.
Figure 6B:
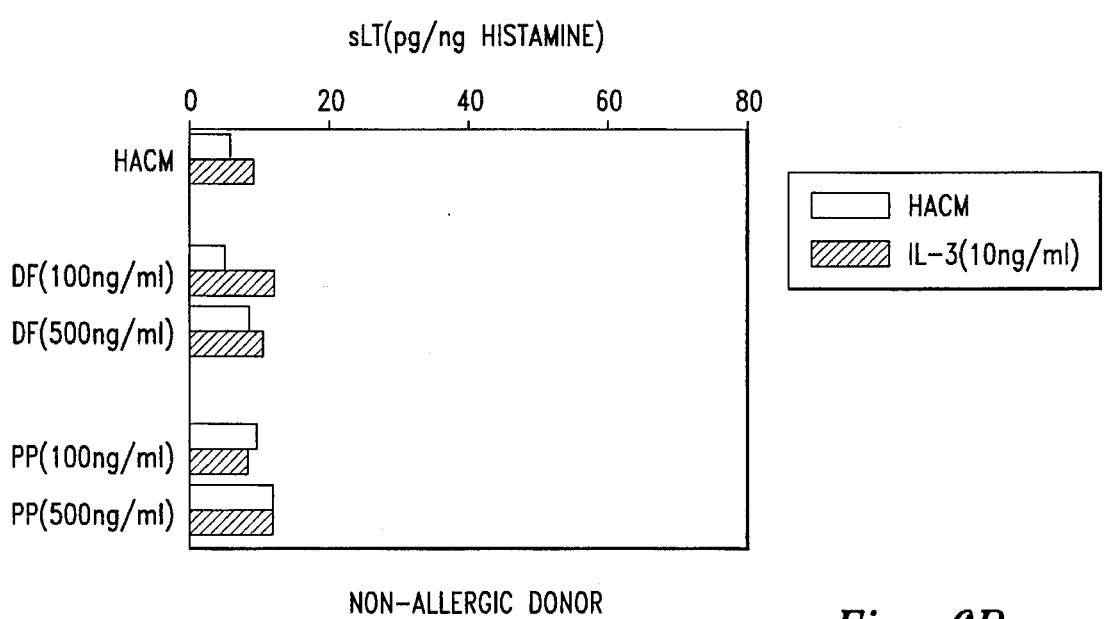

FIGS. 6A and 6B show the ELISA detection of allergen-triggered-sLT generation in whole blood. Heparinized blood (25 µl/well) from a mite allergic donor (FIG. 6A)

and an non-allergic donor (FIG. 6B) was stimulated with *Dermatophagoides farinae* (DF) or *Phleum pratense* (PP) extract, with (solid columns) or without (open columns) prior addition of IL-3 (10 ng/ml). Supernatants were harvested after 40 min at 37° C. and sLT content was measured by ELISA as detailed in the present specification. Data are means of duplicates with ranges <15%. For easy comparison, sLT are given with reference to total histamine present in the sample, a measure of blood basophil content, i.e. as pg sLT per total amount of histamine (ng)

The results shown in FIG. 6 reflect sLT generation by approximately 100–300 basophils and are in the range expected from experiments with isolated MNC. As shown in FIG. 7, there is an excellent correlation between the results obtained with diluted whole blood and with isolated MNC.

Figure 7A:
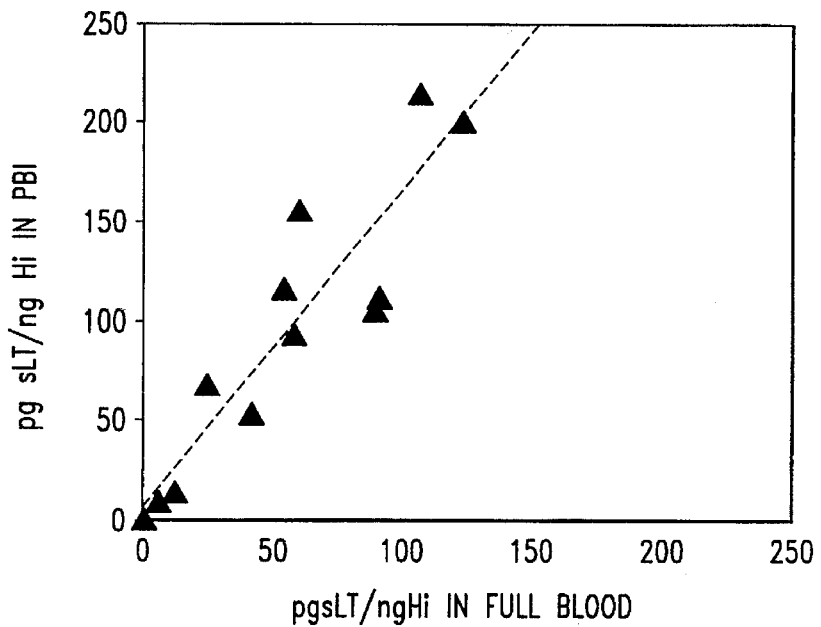
FIGS. 7A and 7B show in a set of two diagrams the correlation between the amount of sLT or histamine generated by mononuclear cells isolated or in whole blood, in 12 individuals; the cells were challenged with anti-IgE antibody.
Figure 7B:
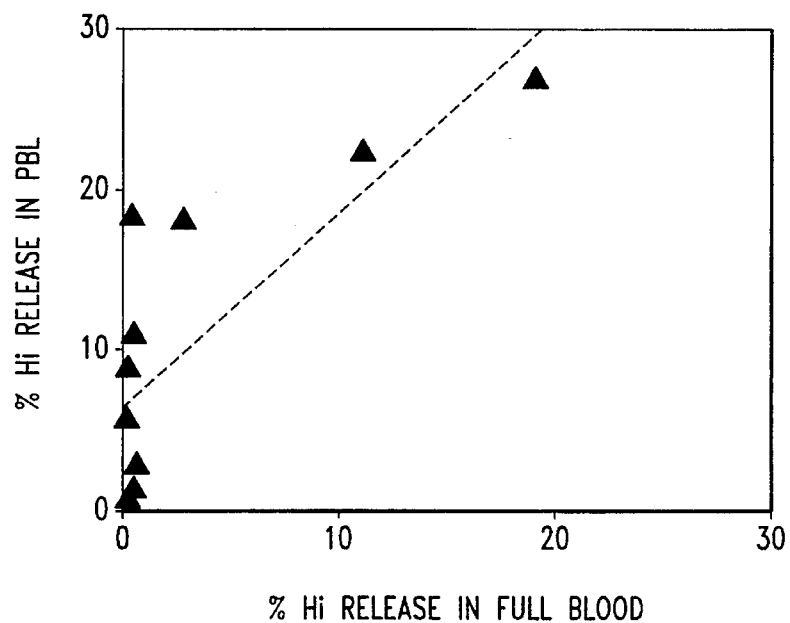

FIG. 7 shows in a set of two diagrams the correlation between the amount of sLT (FIG. 7A) or histamine (FIG.7B) generated by mononuclear cells isolated (PBL) or in full blood, in 12 individuals; the cells were challenged with anti-IgE antibody 100 µg/ml.

This is in contrast to the experience made with histamine release performed in parallel on the same supernatants. There, the correlation is much less impressive, obviously due to interference of some cells and/or plasma proteins with histamine determination. This observation underlines the unique position of the sLT ELISA assay for detection of allergen-induced reactions in whole blood.

Figure 8A:
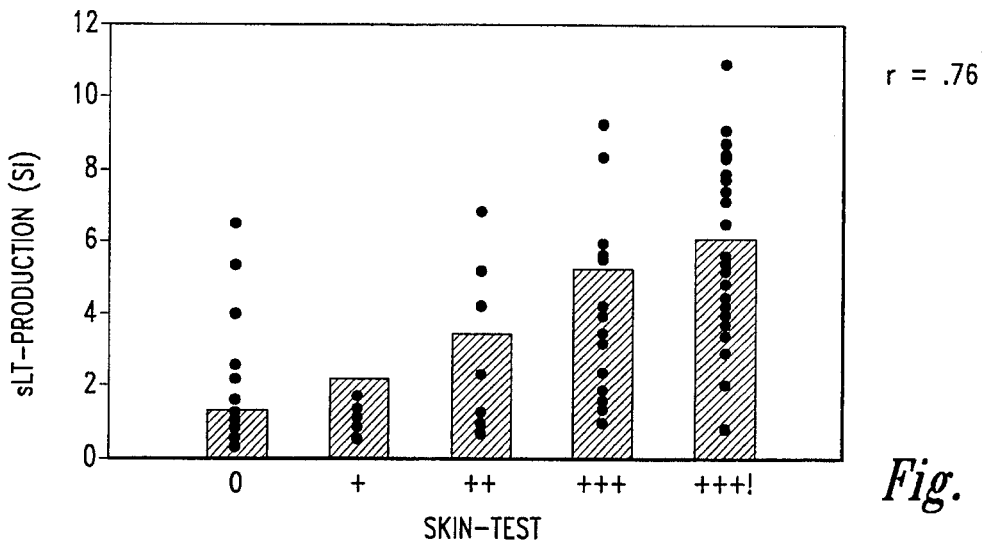
FIGS. 8A, 8B and 8C show in a set of three diagrams the comparison of skin test, RAST and sLT production from 38 patients tested with 5 allergens. (6-Grasses, Birch, *D.pt. eronyssinus,* Mugwort, Plantain).
Figure 8B:
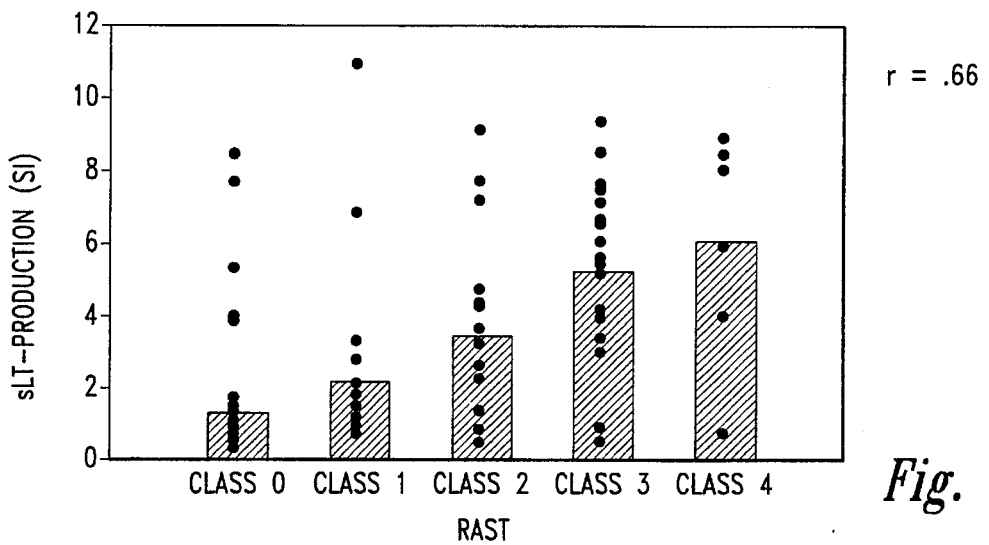
Figure 8C:
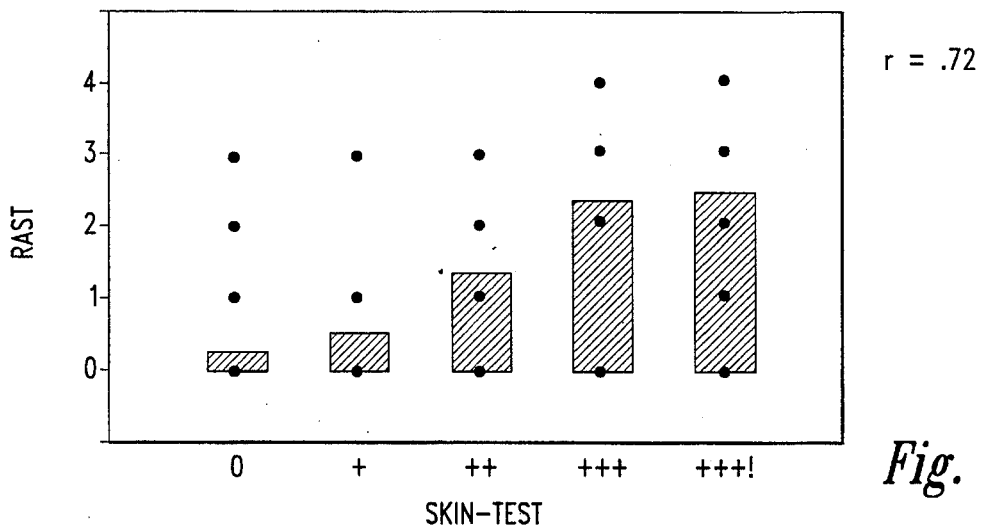
Figure 9:
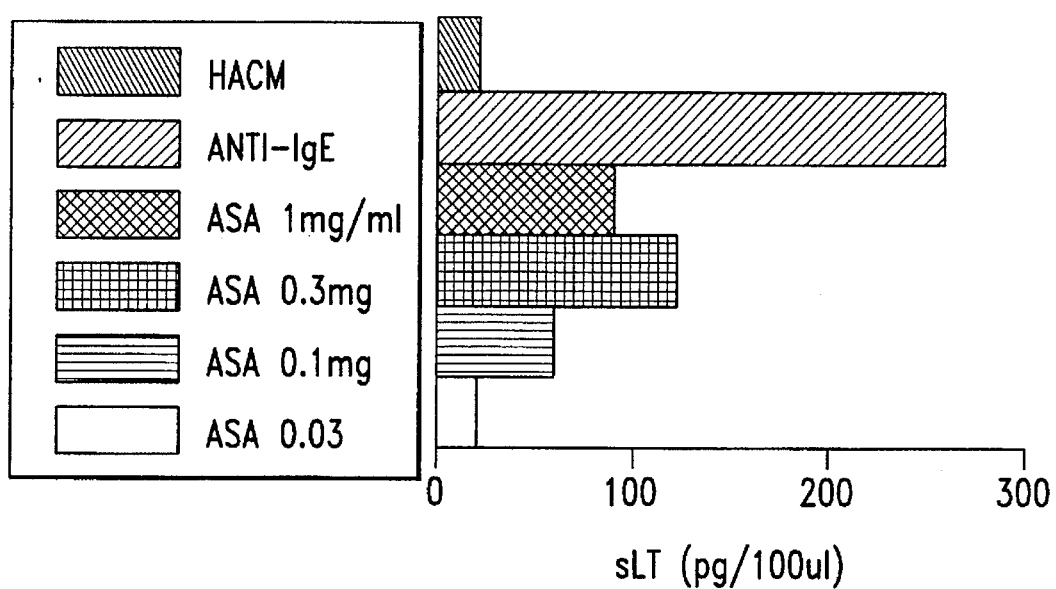
FIG. 9 shows in a diagram the sLT production of an aspirin-sensitive patient upon challenge with acetylsalicylic acid (ASA) in the sLT assay.

FIGS. 8A, 8B and 8C show in a set of three diagrams the comparison of skin-test, RAST and sLT production from 38 patients tested with 5 allergens. (6-Grasses, Birch, *D.pt. eronyssinus*, Mugwort, Plantain). The results obtained in parallel with skin tests and with the classical serological PAST assay for allergen-specific IgE show that there is a better correlation between the sLT assay and the skin test, and hence with the clinical status of the patient, than between the RAST assay and the skin test. This shows that the theoretical advantage of using a cellular assay for detecting allergic hypersensitivity is for the first time confirmed in practice. The possibility to diagnose pseudo-allergies, in which no IgE antibodies are serologically detectable, is also confirmed by results showing the release of sLT upon challenge with aspirin (ASA) (FIG. 9). The capacity of the cells to produce sLT upon challenge is always checked with a monoclonal anti-IgE antibody (Le 27, positive control, FIG. 9).

Although the results shown here have been obtained upon addition of allergen in fluid phase, similar results may be obtained by addition of allergen on solid phase, either as coat on the bottom of the wells used for the first incubation with cells or as allergen-coated cellulose disks and/or plastic beads, microprecipitates, etc. (Table 1).

TABLE 1

Production of sLT upon challenge with allergens in various forms.

| Allergen | Total allergen added | Nb cells/well (MNC) | sLT in pg/100 µl |
|---|---|---|---|
| D. pteronyssinus in fluid form | 10 ng | $10^5$ | 65–150 (n = 5) |
| D. pteronyssinus on disk | 8 ng | $10^5$ | 40–120 (n = 3) |
| D. pteronyssinus adsorbed on well | 5 ng | $10^5$ | 55–130 (n = 3) |

This is meaningful since it enables preparations diagnostic kits with multiple allergens in a more economical and practical fashion than when using a battery of allergens in solution.

EXAMPLE 4

Figure 1A:
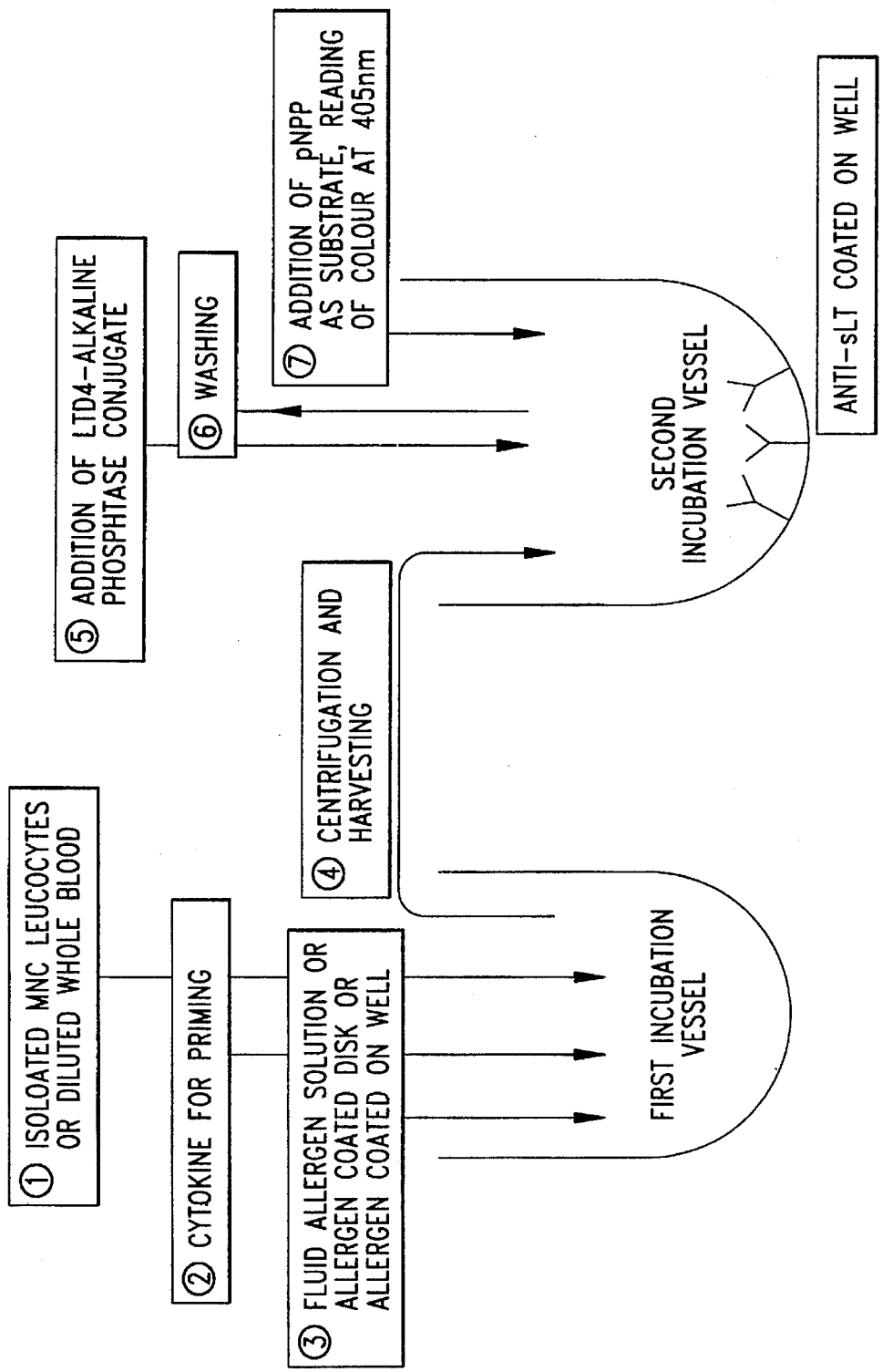
FIGS. 1A and 1B show diagrammatic drawings of a one-step and a two-step sLT-ELISA-Test, respectively, for its use in the diagnosis of allergies and inflammatory diseases.

One Step Assay for the Detection of sLT Generated by Allergen-exposed Isolated Mononuclear Cells or Diluted Whole Blood by ELISA In the two-step assay described in FIG. 1a and Example 3, the preincubation of isolated MNC or of whole blood cells with priming lymphokines followed by incubation with allergens or non specific stimulants takes place in a first series of separate containers and requires a centrifugation step in order to harvest supernatants. These supernatants are then analyzed in a second microtiterplate prepared for performance of the sLT-ELISA.

In the one-step assay to be described now, all operations take place in the same microtiter-plate and the centrifugation and harvesting steps are avoided, making the test more practical and economical.

Figure 1B:
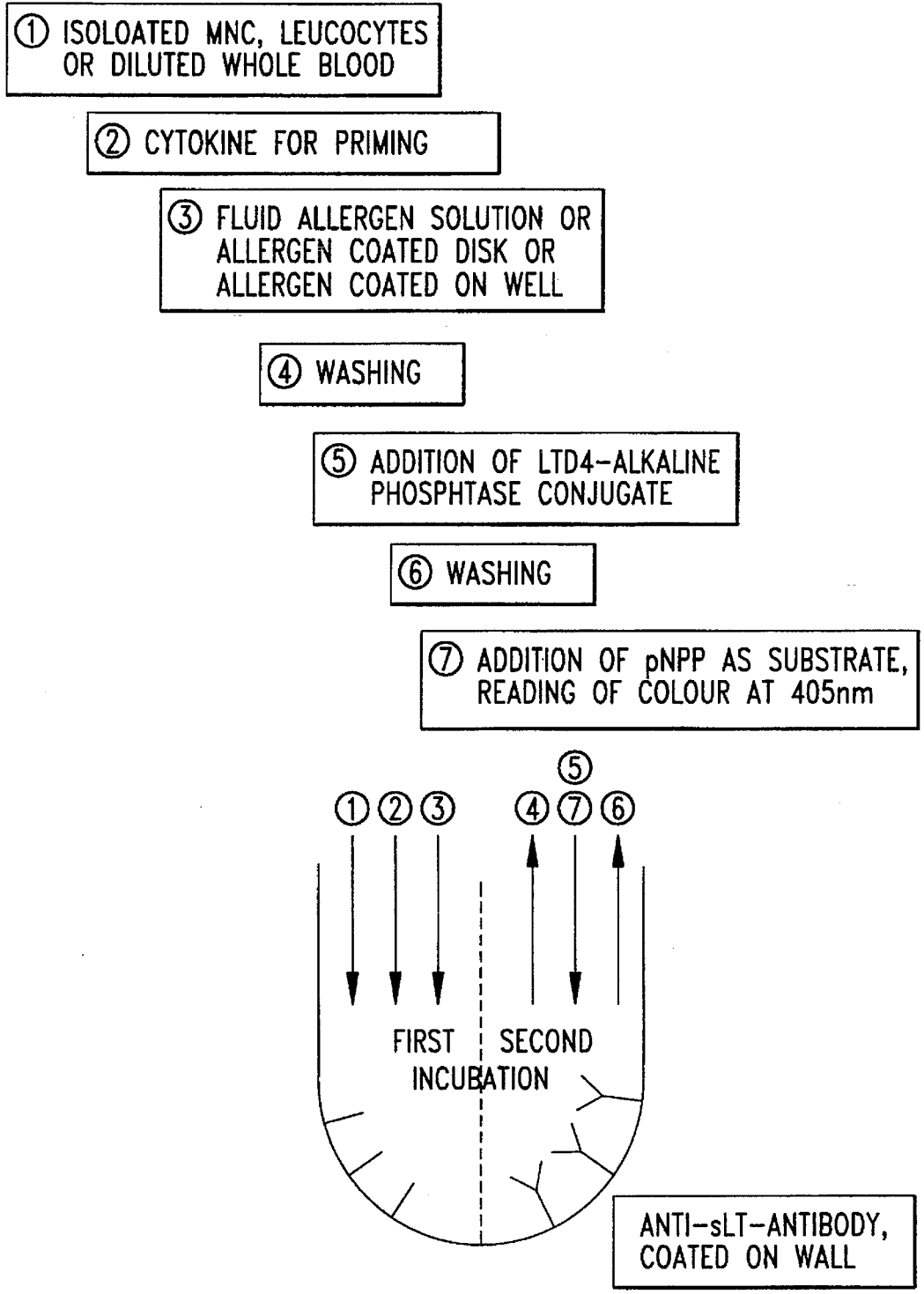

As shown in FIG. 1b, the microtiterplate needed For the sLT-ELISA and precoated with anti-sLT antibody are also simultaneously precoated with the intended stimulating agent, for example by allergens or allergen mixtures. In this way, the number and succession of operations needed are:
(a) Addition of isolated MNC or diluted whole blood
(b) Addition of priming cytokine, such as IL 3 and prolonged incubation
(c) Washing without centrifugation step
(d) Addition of LTD4-AP conjugate
(e) Reading in densitometer The operations are markedly reduced and simplified; they also all take place in the same container. This results in a considerable gain in material, time and simplicity of operation, without affecting the quality of the results needed for clinical diagnosis.

The detailed procedures and concentrations of reagents used follow the indications given in Examples 2 and 3. An example of results obtained by the one step method is given in Table 2.

TABLE 2

Results from one-step sLT Assay

| Allergen | Total allergen given (fluid) | Number cells/well (blood) | sLT in pg/100 µl |
|---|---|---|---|
| 1. *D. pteronyssinus* | | | |
| Allergic patients | 10 ng | $3 \times 10^5$ | 30–140 (n = 4) |
| Non allergic patients | 10 ng | $3 \times 10^5$ | 0–10 (n = 4) |
| 2. Timothy pollen | | | |
| Allergic patients | 5 ng | $2 \times 10^5$ | 45–180 (n = 5) |
| Non allergic patients | 5 ng | $2 \times 10^5$ | 0–10 (n = 4) |

The only limitation to the generalized use of this one step assay may be due to interference between the allergens coated in the wells and some of the reagents involved, in particular with serum antibodies present in excess and which may neutralize the allergens. In that case, the use of allergen-coated disks and/or a centrifugation step to remove plasma proteins may prove necessary.

Whatever the final form of the assay, the sLT-ELISA assay in the forms described represents the first type of cellular allergy diagnostic assay clearly suitable for economic and efficient in vitro allergy diagnosis.

EXAMPLE 5

Use of the sLT-ELISA Assay for Diagnostic Purposes in Inflammatory and Immunodeficiency Diseases Using the general schemes indicated in Examples 2, 3 and 4, it is possible to evaluate the reactivity of inflammatory blood cells or of tissue and biological fluid cells, either by following their spontaneous generation of sLT or by challenging them with a variety of non specific stimulants, such as ionomycin, the complement component C5a or the bacterial-related fMLP. By choosing the appropriate stimulant, the reactivity of subpopulations of cells, even when using diluted whole blood, can also be assessed.

Figure 10:
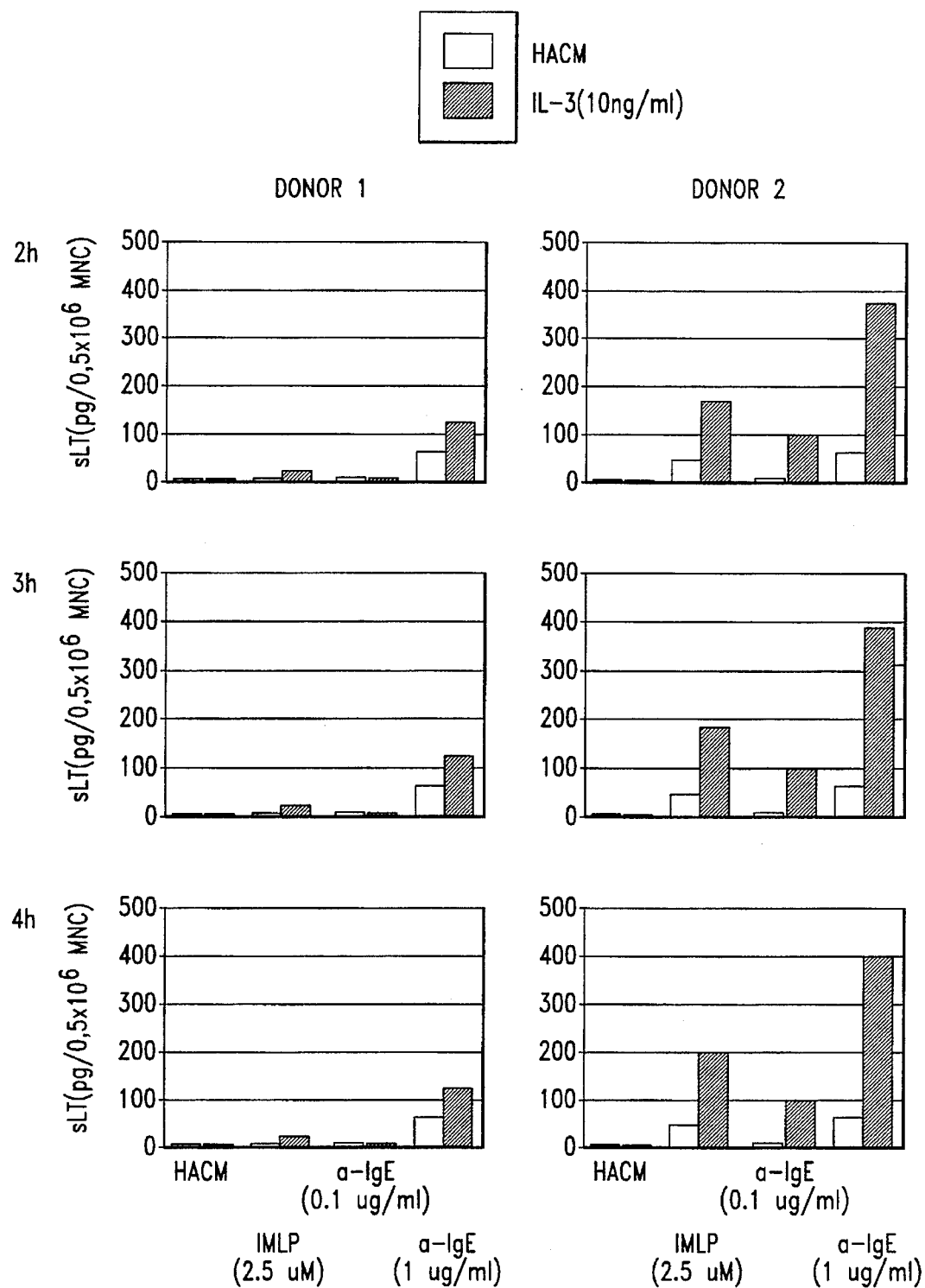
FIG. 10 shows in a set of diagrams the comparison of the sLT release in IL3-primed and untreated (HACM alone) diluted whole blood of two donors after 2, 4 and 6 h; the cells were specifically challenged with fMLP or anti-IgE antibodies.

FIG. 10 shows in a set of diagrams the comparison of the sLT release in IL3-primed and untreated (HACM alone) diluted whole blood of two donors after 2, 4 and 6 h; the cells were specifically challenged with fMLP or anti-IgE antibodies.

FIG. 10 shows the reactivity of various donors to the fMLP stimulant as well as the priming effect of pretreatment of the MNC with IL 3. Since the evolution and stage of activity of inflammatory diseases as well as some states of immune deficiency are reflected by cellular hyper- or hyporeactivity, respectively, the sLT-ELISA test may be expected to play a useful role in the diagnosis and monitoring of such diseases.

I claim:

1. A method for assessing cellular hypersensitivity of a human being to a stimulating agent comprising the following steps:
    a) contacting a sample derived from the human being comprising one or more of the group consisting of basophils and leukocytes with a cytokine selected from the group consisting of IL3, IL5, GM-CSF and NGF under conditions suitable for said cytokine to prime said basophils or leukocytes, to provide a primed sample;
    b) contacting said primed sample with a stimulating agent under conditions suitable for said stimulating agent to challenge said basophils or leukocytes, thereby causing said basophils or leukocytes to release one or more sulfidoleukotrienes (sLT) selected from the group consisting of LTC4, LTD4 and LTE4 if said basophils or leukocytes are sensitive to said stimulating agent, to provide a challenged sample;
    c) contacting said challenged sample with a solid phase carrier-bound monoclonal antibody which specifically binds said sLT under conditions suitable for binding between said antibody and said sLT in said challenged sample;
    d) adding an enzyme-labeled sulfidoleukotriene selected from the group consisting of LTC4, LTD4 and LTE4 to the challenged sample and said antibody; and
    e) evaluating an amount of the enzyme-labeled sulfidoleukotriene bound to the carrier by an immunoenzymatic ELISA assay, and thereby determining the cellular hypersensitivity of the human being to said stimulating agent, said amount being in inverse proportion to an amount of released sLT bound to said carrier.

2. A method according to claim 1 wherein said cytokine is selected from the group consisting of IL3, IL5 and GM-CSF.

3. A method according to claim 1 wherein said sample comprises unpurified biological fluid.

4. A method according to claim 3 wherein said sample comprises whole blood, synovial fluid or urine.

5. A method according to claim 4 wherein said sample comprises whole blood.

6. A method according to claim 1 wherein said sample comprises a suspension of leukocytes, a suspension of mononuclear cells or a supernatant of a cell culture.

7. A method according to claim 1 wherein steps a) through e) are repeated simultaneously with multiple samples and wherein said carrier is a microtiter plate.

8. A method according to claim 1 wherein steps a) through e) are repeated simultaneously with multiple samples and wherein said carrier is a strip device.

9. A method according to claim 1 wherein said antibody is bound to a carrier selected from the group consisting of a microtiter plate and a strip device.

10. A method according to claim 9 wherein said antibody is bound directly to said carrier by glutaraldehydes, polylysine or a biotin-avidin coupling system, or indirectly by an anti-mouse IgG antibody.

11. A method according to claim 1 wherein the stimulating agent is added in a liquid form or in a carrier bound form.

12. A method according to claim 1 wherein the complete procedure is carried out in a single reaction vessel.

13. A method according to claim 8 or 9 wherein the complete procedure for each sample is carried out in a single reaction vessel.

14. A method according to claim 1 wherein step a) is carried out in a separate reaction vessel.

15. A method according to claim 1 wherein the enzyme-labeled sulfidoleukotriene is conjugated to a label selected from the group consisting of alkaline phosphatase, horseradish peroxidase and cholinesterase.

16. A method according to claim 1 wherein said sample comprises from 5 µl to 1000 µl.

17. A method according to claim 1 wherein said sample comprises from 10 µl to 25 µl.

18. A method according to claim 1 wherein said stimulating agent is an allergen.

19. A method according to claim 1 wherein said stimulating agent is a pseudo-allergen.

20. A kit of reagents for a diagnostic in vitro assay for assessing cellular hypersensitivity of a human being to a stimulating agent comprising,
    a) a microtiter plate having wells that are coated with monoclonal anti-sLT which specifically bind sLT antibodies,
    b) a cytokine selected from the group consisting of IL3, IL5, GM-CSF and NGF; and
    c) an enzyme-labeled sulfidoleukotriene selected from the group consisting of LTC4, LTD4 and LTE4.

21. A kit according to claim 20 wherein said microtiter plate is coated partially with monoclonal antibodies which specifically bind sLT and partially with a stimulating agent.

22. A kit according to claim 20 wherein said cytokine is selected from the group consisting of IL3, IL5, and GM-CSF.

* * * * *